United States Patent [19]

Fujita et al.

[11] Patent Number: 5,254,766
[45] Date of Patent: Oct. 19, 1993

[54] PROCESS FOR PRODUCING ALKYL-SUBSTITUTED AROMATIC HYDROCARBON USING HETEROPOLYACID SALTS

[75] Inventors: Terunori Fujita, Ohtake; Kazunori Takahata, Hatsukaichi; Hiroyasu Ohno, Hiroshima; Masayasu Ishibashi, Yamaguchi; Hideo Oikawa, Iwakuni, all of Japan

[73] Assignee: Mitsui Petrochemical Industries, Ltd., Tokyo, Japan

[21] Appl. No.: 773,264

[22] Filed: Oct. 9, 1991

[30] Foreign Application Priority Data

| Oct. 16, 1990 | [JP] | Japan | 2-277026 |
| Mar. 14, 1991 | [JP] | Japan | 3-049710 |
| Mar. 14, 1991 | [JP] | Japan | 3-049711 |
| Jul. 19, 1991 | [JP] | Japan | 3-179283 |
| Jul. 22, 1991 | [JP] | Japan | 3-204546 |
| Jul. 22, 1991 | [JP] | Japan | 3-204547 |

[51] Int. Cl.$^5$ .............................................. C07C 2/70
[52] U.S. Cl. .................................. 585/467; 585/446; 585/466
[58] Field of Search .................. 585/466, 467, 446

[56] References Cited

U.S. PATENT DOCUMENTS

| 2,773,921 | 12/1956 | Rylander et al. | 585/466 |
| 3,346,657 | 10/1967 | Heuke et al. | 585/455 |
| 4,094,922 | 6/1978 | Bartek et al. | 585/460 |
| 4,689,436 | 8/1987 | Minokami et al. | 585/422 |

FOREIGN PATENT DOCUMENTS 0440250 8/1991 European Pat. Off.
1221135 10/1986 Japan.

Primary Examiner—Asok Pal
Assistant Examiner—P. Achutamurthy
Attorney, Agent, or Firm—Birch, Stewart, Kolasch & Birch

[57] ABSTRACT

A process for producing an alkyl-substituted aromatic hydrocarbon, which comprises alkylating an aromatic hydrocarbon with an alkylating agent in the presence of a heteropoly-acid or a salt thereof such as phosphorus tungstate and silicon tungstate as a catalyst. The process is particularly useful for preparing alkyl-substituted naphthalene or naphthalene derivatives.

11 Claims, 1 Drawing Sheet

5,254,766

PROCESS FOR PRODUCING ALKYL-SUBSTITUTED AROMATIC HYDROCARBON USING HETEROPOLYACID SALTS

BACKGROUND OF THE INVENTION

The present invention relates to a process for producing an alkyl-substituted aromatic hydrocarbon. More specifically, it relates to a process for producing an alkyl-substituted aromatic hydrocarbon at high yields industrially advantageously.

An alkyl-substituted aromatic hydrocarbon is useful as an intermediate for the preparation of a polymer and medicaments. As a process for producing such an alkyl-substituted aromatic hydrocarbon, there are conventionally known the Friedel-Crafts reaction in which an aromatic hydrocarbon is alkylated in a liquid phase in the presence of anhydrous aluminum chloride as a catalyst, a gaseous-phase reaction in which an aromatic hydrocarbon is alkylated in the presence of a solid silica alumina as a catalyst, or the like.

Since, however, the Friedel-Crafts reaction generally produces a large amount of high-boiling compound(s) as a by-product, the intended alkyl-substituted aromatic hydrocarbon cannot be produced at high yields. The other gaseous phase reaction using a solid silica alumina catalyst requires a high temperature, and various side reactions occur. Therefore, the yield of the intended product is similarly low.

The Mar. 6, 1991 issue of Nikkan Kogyo Shinbun (The Business and Technology Daily News) reported that when an acidic catalyst prepared by partially replacing hydrogen in tungstophosphoric acid with cesium is used in the production of dodecylphenol from phenol, it exhibits 20 to 60 times greater activity than sulfuric acid (catalyst) per weight and 100 times higher activity than zeolite per weight. This report also said that even a potassium salt, too, is considered effective as catalyst.

SUMMARY OF THE INVENTION

It is an object of the present invention to provide an industrially advantageous process for producing an alkyl-substituted aromatic hydrocarbon.

It is another object of the present invention to provide a process for producing an alkyl-substituted aromatic hydrocarbon at high yields industrially advantageously by alkylating an aromatic hydrocarbon such as naphthalenes and alkyl naphthalenes with an alkylating agent in the presence of a catalyst while inhibiting the formation of high-boiling by-products under mild conditions.

The above objects and other objects and advantages of the present invention will be apparent from the following description.

According to the present invention, the above objects and advantages are achieved by a process for producing an alkyl-substituted aromatic hydrocarbon, which comprises alkylating an aromatic hydrocarbon with an alkylating agent in the presence of a heteropoly-acid or salt thereof as a catalyst.

DETAILED DESCRIPTION OF THE INVENTION

Figure 1:
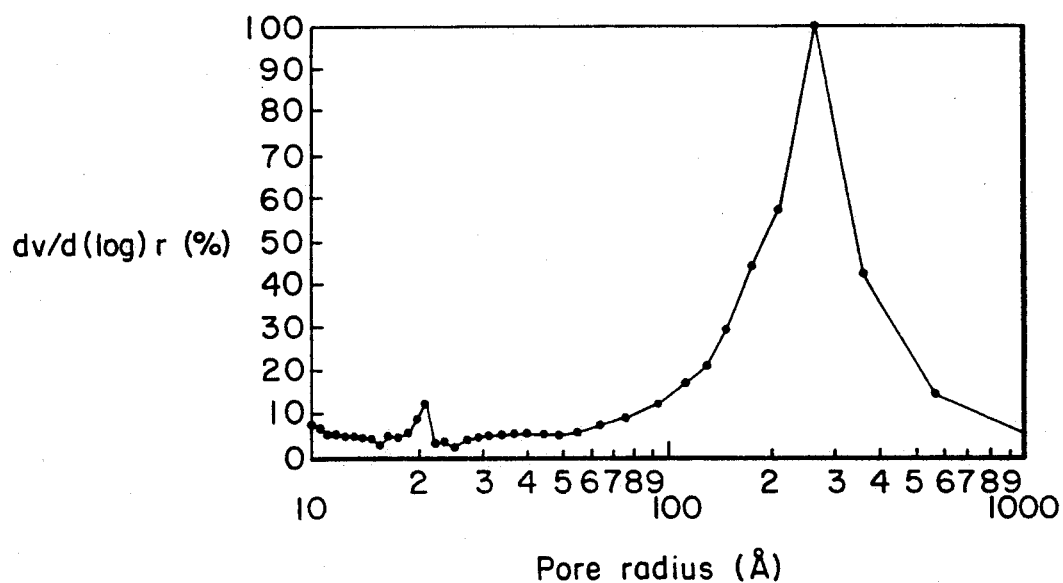
FIG. 1 is a pore distribution curve of the catalyst used in Example 32.

In the present invention, the aromatic hydrocarbon as a raw material for the alkylation may be any one of monocyclic, polycyclic and fused-ring aromatic hydrocarbons of which the aromatic rings have a substitution position for the alkylation. The aromatic hydrocarbon includes monocyclic compounds such as benzene, polycyclic compounds such as biphenyl and diphenyl methane and fused-ring compounds such as naphthalene and anthracene. These compounds may have one or more substituents on the aromatic ring. The substituent includes, for example a halogen atom, an alkyl group and a haloalkyl group.

The halogen atom preferably includes, e.g., fluorine, chlorine and bromine.

The alkyl group may be linear or branched, and preferably includes those having 1 to 8 carbon atoms such as methyl, ethyl, n-propyl, iso-propyl, n-butyl and isobutyl.

The haloalkyl group preferably includes groups in which a halogen atom such as fluorine or chlorine is substituted on the above alkyl groups having 1 to 8 carbon atoms, such as fluoromethyl.

As an aromatic hydrocarbon, particularly preferred are naphthalenes. Such naphthalenes include naphthalene; methylnaphthalenes such as 1-methyl-naphthalenes and 2-methylnaphthalene; dimethylnaphthalenes such as 1,5-dimethylnaphthalene and 1,6-dimethylnaphthalene; ethylnaphthalenes such as 1-ethylnaphthalene and 2-ethylnaphthalene; diethylnaphthalenes such as 2,6-diethylnaphthalene and 2,3-diethylnaphthalene; trimethylnaphthalenes such as 1,3,6-trimethylnaphthalenes; isopropylnaphthalenes such as 1-isopropylnaphthalene and 2-isopropylnaphthalene; and naphthalenes having a combination of alkyl group members such as methylethylnaphthalene, methylisopropylnaphthalene, ethylisopropylnaphthalene, dimethylethylnaphthalene, methyldiethylnaphthalene, dimethyldiethylnaphthalene, dimethyldiisopropylnaphthalene, trimethylethylnaphthalene, trimethyldiethylnaphthalene and diethylisopropylnaphthalene.

Of the above naphthalenes, particularly preferred in the present invention are naphthalene and mono- or dialkylnaphthalenes having one or two alkyl group members selected from methyl, ethyl and isopropyl. Specific examples of such naphthalenes include methylnaphthalenes, ethylnaphthalenes, dimethylnaphthalenes and isopropylnaphthalenes in addition to naphthalene.

Examples of the alkylating agent includes α-olefins such as $C_2$–$C_{20}$ monoolefins, e.g. ethylene and propylene; aliphatic lower alcohols such as ethanol and isopropyl alcohol; lower alkyl ethers such as ethyl ether and isopropyl ether; acetic acid lower alkyl esters such as ethyl acetate and isopropyl acetate; and alkyl halides such as methyl chloride and isopropyl chloride, particularly lower alkyl chlorides generally used for alkylation; and polyalkylbenzenes such as diethylbenzene, triethylbenzene, tetraethylbenzene, diisopropylbenzene, triisopropylbenzene, tetraisopropylbenzene and mixtures of these used for transalkylation.

Of the above alkylating agents, particularly preferred are α-olefins.

In the process of the present invention, a heteropolyacid or a salt thereof is used as a catalyst when the above aromatic hydrocarbon is alkylated with the above alkylating agent.

The heteropoly-acid or the salt thereof preferably includes, e.g., phosphorus tungstic acid, phosphorus molybdic acid, silicotungstic acid, silicomolybdic acid, and a compound obtained by replacing part or all of protons of any one of these acids with metals belonging to the group Ia of the periodic table (alkali metals) or metals belonging to the group IIa of the periodic table (alkaline earth metals).

Examples of the alkali metals are cesium, sodium, potassium, rubidium and lithium. Examples of the alkaline earth metals are magnesium, calcium, strontium and barium.

Of these catalysts, phosphorus tungstic acid, silicotungstic acid and salts of these are more preferably used.

As a phosphorus tungstic acid or a salt thereof, preferred is a compound of the formula (1), $$M_xH_{3-x}PW_{12}O_{40} \quad (1)$$

wherein M is a metal belonging to the group Ia of the periodic table, and x is a number of 0 to 2.8.

A compound of the formula (1) in which x is 0.5 to 2.8 is more preferred, and a compound of the formula (1) in which x is 1.0 to 2.5 is particularly preferred. As a metal M belonging to the group Ia of the periodic table, preferred is potassium, rubidium or cesium.

The salt of phosphorus tungstic acid may include a complex salt obtained by replacing hydrogen atoms of phosphorus tungstic acid with a plurality of the above metals which are different from each other in kind.

Phosphorus tungstic acid or a salt thereof often contains crystal water. In the present specification, the description of such crystal water is omitted. That is, the description of no crystal water in the present specification does not necessarily mean the absence of crystal water.

Such a metal salt of phosphorus tungstic acid can be obtained by adding a stoichiometric amount of a carbonate of metal(s) belonging to the group Ia of a the periodic table to an aqueous solution of phosphorus tungstic acid with stirring and then subjecting the mixture to evaporation and solidification, e.g., at 50° C.

Further, the present inventors' study has showed that the catalyst obtained by bringing an aqueous solution of phosphorus tungstic acid and solid potassium carbonate to contact with each other particularly exhibits excellent activity.

For the preparation of the above metal salt of phosphorus tungstic acid, the aqueous solution of phosphorus tungstic acid as a $H_3PW_{12}O_{40}$ preferably has a concentration of 10 to 150 g/100 cc, more preferably 30 to 100 g/100 cc.

The solid potassium carbonate may be any one of 1.5-hydrate or dihydrate.

An aqueous solution of phosphorus tungstic acid and solid potassium carbonate may be brought into contact with each other, e.g., by any one of a method in which solid potassium carbonate is added to an aqueous solution of phosphorus tungstic acid and a method in which an aqueous solution of phosphorus tungstic acid is added to solid potassium carbonate. Preferred is the method in which solid potassium carbonate is added to an aqueous solution of phosphorus tungstic acid.

The precipitate of potassium phosphorus tungstate obtained by the contact of an aqueous solution of phosphorus tungstic acid and solid potassium carbonate is concentrated, preferably concentrated under reduced pressure, to form potassium phosphorus tungstate.

The temperature for bringing an aqueous solution of phosphorus tungstic acid and solid potassium carbonate into contact with each other is preferably between 5° C. and 50° C.

The present inventors' study has also showed the following: According to a method in which potassium carbonate in the form of a solid or an aqueous solution is gradually added to an aqueous solution of phosphorus tungstic acid and the reaction mixture is subjected to dehydration by distillation under reduced pressure, there can be obtained a catalyst having numerous pores having an average pore radius of 100 to 600 Å, preferably 200 to 500 Å, and this catalyst also exhibits remarkably superior activity.

As a heteropoly-acid or the salt thereof in the present invention, silicotungstic acid or an acid thereof is also used. As silicotungstic acid or an acid thereof, preferred is a compound of the formula (2), $$M_xH_{4-x}SiW_{12}O_4 \quad (2)$$

wherein M and x are as defined above.

A compound of the formula (2) in which x is 0.5 to 2.8 is more preferred, and a compound of the formula (2) in which x is 1.0 to 2.5 is particularly preferred. In the formula (2), potassium, rubidium or cesium is preferred as a metal (M) belonging to the group Ia of the periodic table.

The salt of silicotungstic acid includes complex salts obtained by replacing hydrogen atoms of silicotungstic acid with a plurality of the above metals which are different from each other in kind.

Silicotungstic acid or a salt thereof often contains crystal water. In the present specification, the description of such crystal water is omitted. That is, the description of no crystal water in the present specification does not necessarily mean the absence of crystal water.

Such a metal salt of silicotungstic acid can be obtained by adding a stoichiometric amount of carbonate of metal(s) belonging to the group Ia of the periodic table to an aqueous solution of silicotungstic acid with stirring and then subjecting the mixture to evaporation and solidification, e.g., at 50° C.

The heteropoly-acid or the salt thereof as a catalyst may be used in an as-produced state as a catalyst. Meanwhile, the heteropoly-acid or the salt thereof may be supported, e.g., on silica gel, activated carbon, silica-alumina, alumina, saponite, montmorillonite, acid clay, activated clay, or titania. Further, the heteropoly-acid or salt thereof may be dried by heating it to 100° to 300° C. to increase its alkylating catalyst activity.

In the process of the present invention, the above-described heteropoly acids or salts thereof may be used alone or in combination.

For the alkylation, the amount of the potassium phosphorus tungstate as an anhydride per part of the aromatic compound as a raw material is preferably 0.0001 to 0.5 part by weight, more preferably 0.001 to 0.1 part by weight. The alkylation can be carried out by any method such as a continuous flow method and a batch method. The reaction conditions are suitably selected depending upon an aromatic compound as a raw material and the kind of an alkylating agent. For example, when olefins are used as an alkylating agent, the reaction is generally carried out in a liquid phase under pressure in the presence or absence of a solvent. The solvent is preferably selected, for example, from saturated hydrocarbons such as decalin, cyclodecane, hexane, heptane, octane, nonane, decane, undecane and dodecane; halogenated aliphatic hydrocarbons such as dichloromethane and 1,2-dichloroethane; halogenated aromatic hydrocarbons such as chlorobenzene, dichlorobenzene, bromobenzene and dibromobenzene; ethers such as diethyl ether and tetrahydrofuran; and carbon disulfide. Of the above solvents, particularly preferred are saturated hydrocarbons. The reaction temperature is preferably between 100° C. and 300° C., more preferably 150° C. and 250° C. The reaction pressure (olefin pressure) is preferably 1 to 500 kg/cm$^2$.G, more preferably 1 to 300 kg/cm$^2$.G.

The reaction time depends on aromatic hydrocarbon as a raw material, a catalyst, amounts of the raw material and the catalyst and a reaction temperature. In general, however, the reaction time is 1 minute to 24 hours, preferably 30 minutes to 10 hours.

After the reaction is carried out in the liquid phase as described above, the catalyst is, for example, separated from the reaction mixture by filtration and the solvent is distilled off, whereby the intended alkyl-substituted aromatic hydrocarbon can be obtained. The alkyl-substituted aromatic hydrocarbon is further treated by distillation, extraction, recrystallization, etc., as required.

According to the present invention, a heteropolyacid or a salt thereof is used as a catalyst as described above in the production of an alkyl-substituted aromatic hydrocarbon by alkylating an aromatic hydrocarbon with an alkylating agent. Therefore, the intended alkylation can be carried out with high selectivity under mild conditions while inhibiting side reactions of the aromatic hydrocarbon as a material and olefins as an alkylating agent in particular, and the intended alkyl-substituted aromatic hydrocarbon can be obtained at high yields.

The present invention will be explained further in detail hereinafter. However, the present invention shall not be limited to these Examples.

EXAMPLE 1

An autoclave having a capacity of 50 ml was charged with 700 mg of naphthalene, 2 ml of n-hexane together with 60 mg of phosphorus tungstic acid which had been preliminarily dried under heat at 200° C. for 3 hours. Then, ethylene was introduced into the autoclave under pressure until the ethylene pressure in the autoclave became 60 kg/cm$^2$G, and the autoclave was closed. The mixture was allowed to react with stirring at 180° C. for 3 hours.

The reaction results are as follows: Naphthalene conversion 100%, selectivity to diethylnaphthalenes 14%, selectivity to triethylnaphthalenes 33%, selectivity to tetraethylnaphthalenes 31%, selectivity to pentaethylnaphthalenes 15%, and tar formation ratio 7%.

EXAMPLE 2

An autoclave having a capacity of 50 ml was charged with 700 mg of naphthalene, 4 ml of a hexane mixture together with 50 mg of phosphorus tungstic acid which had been preliminarily dried under heat at 200° C. for 3 hours. Then, ethylene was introduced into the autoclave under pressure until the ethylene pressure in the autoclave became 30 kg/cm$^2$G, and the autoclave was closed. The mixture was allowed to react with stirring at 170° C. for 2 hours.

The reaction results are as follows: Naphthalene conversion 72%, selectivity to monoethylnaphthalenes 29%, selectivity to diethylnaphthalenes 42%, selectivity to triethylnaphthalenes 18%, and tar formation ratio 2%.

EXAMPLE 3

Example 2 was repeated except that the phosphorus tungstic acid was replaced with 200 mg of a catalyst in which 25% by weight of phosphorus tungstic acid was supported on silica (Wako Gel C-200), and which had been preliminarily dried under heat at 200° C. for 3 hours.

The reaction results are as follows: Naphthalene conversion 58%, selectivity to monoethylnaphthalenes 20%, selectivity to diethylnaphthalenes 51%, selectivity to triethylnaphthalenes 18%, and tar formation ratio 2%.

EXAMPLE 4

Phosphorus tungstic acid ($H_{0.5}Cs_{2.5}PW_{12}O_{40}$) in which protons were partially replaced with cesium was prepared according to the method described in J. Catal., 83, 121 (1983), and this phosphorus tungstic acid was dried under heat at 200° C. for 3 hours.

Then, Example 2 was repeated except for the use of the above phosphorus tungstic acid substituted partially with cesium.

The reaction results are as follows: Naphthalene conversion 67%, selectivity to monoethylnaphthalenes 22%, selectivity to diethylnaphthalenes 46%, selectivity to triethylnaphthalenes 21%, and tar formation ratio 3%.

EXAMPLE 5

Example 2 was repeated except that the phosphorus tungstic acid was replaced with phosphorus molybdic acid which had been preliminarily dried under heat at 200° C. for 3 hours and that the reaction temperature was changed to 220° C.

The reaction results are as follows: Naphthalene conversion 54%, selectivity to monoethylnaphthalenes 19%, selectivity to diethylnaphthalenes 50%, selectivity to triethylnaphthalenes 22%, and tar formation ratio 5%.

EXAMPLE 6

Example 5 was repeated except that the phosphorus molybdic acid was replaced with 70 mg of silicotungstic acid which had been preliminarily dried under heat at 200° C. for 3 hours.

The reaction results are as follows: Naphthalene conversion 48%, selectivity to monoethylnaphthalenes 20%, selectivity to diethylnaphthalenes 48%, selectivity to triethylnaphthalenes 18%, and tar formation ratio 3%.

EXAMPLE 7

A 50 ml autoclave was charged with 700 mg of naphthalene and 2 ml of n-hexane together with 60 mg of a commercially available phosphorus tungstic acid (not dried under heat). Then, ethylene was introduced into the autoclave under pressure until the ethylene pressure in the autoclave became 30 kg/cm$^2$G, and the autoclave was closed. The mixture was allowed to react with stirring at 190° C. for 3 hours.

The reaction results are as follows: Naphthalene conversion 37%, selectivity to monoethylnaphthalenes 62%, selectivity to diethylnaphthalenes 22%, selectivity to triethylnaphthalenes 11%, and tar formation ratio 3%.

EXAMPLE 8

Example 7 was repeated except that naphthalene was replaced with 720 mg of 2-methylnaphthalene.

The reaction results are as follows: 2-Methylnaphthalene conversion 54%, selectivity to methylethylnaphthalenes 30%, selectivity to methyldiethylnaphthalenes 41%, selectivity to methyltriethylnaphthalenes 22%, and tar formation ratio 3%.

EXAMPLE 9

Example 7 was repeated except that naphthalene was replaced with 730 mg of 2-ethylnaphthalene.

The reaction results are as follows: 2-Ethylnaphthalene conversion 60%, selectivity to diethylnaphthalenes 31%, selectivity to triethylnaphthalenes 30%, selectivity to tetraethylnaphthalenes 21%, and tar formation ratio 4%.

EXAMPLE 10

Example 7 was repeated except that naphthalene was replaced with 750 mg of 2-isopropylnaphthalene.

The reaction results are as follows: 2-Isopropylnaphthalene conversion 56%, selectivity to isopropylethylnaphthalenes 32%, selectivity to isopropyldiethylnaphthalenes 29%, selectivity to isopropyltriethylnaphthalenes 20%, and tar formation ratio 4%.

EXAMPLE 11

Example 7 was repeated except that naphthalene was replaced with 730 mg of 2,6-dimethylnaphthalene.

The reaction results are as follows: 2,6-Dimethylnaphthalene conversion 71%, selectivity to dimethylethylnaphthalenes 24%, selectivity to dimethyldiethylnaphthalenes 45%, selectivity to dimethyltriethylnaphthalenes 23%, and tar formation ratio 3%.

EXAMPLE 12

Example 11 was repeated except that the phosphorus tungstic acid was replaced with 200 mg of a catalyst in which 20% by weight of phosphorus tungstic acid was supported on activated carbon and which had been preliminarily dried under heat at 200° C. for 3 hours.

The reaction results are as follows: 2,6-Dimethylnaphthalene conversion 80%, selectivity to dimethylethylnaphthalenes 22%, selectivity to dimethyldiethylnaphthalenes 46%, selectivity to dimethyltriethylnaphthalenes 25%, and tar formation ratio 2%.

EXAMPLE 13

Example 11 was repeated except that the phosphorus tungstic acid was replaced with 200 mg of a catalyst in which 40% by weight of phosphorus tungstic acid was supported on activated clay and which had been preliminarily dried under heat at 200° C. for 3 hours.

The reaction results are as follows: 2,6-Dimethylnaphthalene conversion 84%, selectivity to dimethylethylnaphthalenes 21%, selectivity to dimethyldiethylnaphthalenes 48%, selectivity to dimethyltriethylnaphthalenes 26%, and tar formation ratio 2%.

EXAMPLE 14

A 50 ml autoclave was charged with 10 g of naphthalene (special-grade reagent, supplied by Wako Jun-yaku Kogyo K. K.) and 10 ml of decane together with 850 mg of potassium phosphorus tungstate having a composition shown in Table 1, and the autoclave was closed. Then, a gas phase inside the autoclave was replaced with ethylene gas, and the mixture was allowed to react with stirring under an ethylene pressure of 30 kg/cm$^2$G at a temperature of 200° C. for 2 hours. After the reaction, the catalyst was separated by filtration, and the resultant reaction mixture was analyzed on its contents by gas chromatography. Table 1 shows the results.

EXAMPLES 15-17

Example 14 was repeated except for the use of a metal salt of phosphorus tungstic acid having a composition shown in Table 1. Table 1 shows the results.

EXAMPLE 18

Example 14 was repeated except that the raw material was changed to purified naphthalene (supplied by Kawasaki Steel Corp.), that catalyst was replaced with 10 mg of potassium phosphorus tungstate having a composition shown in Table 1, and further that the reaction temperature was changed to 260° C. Table 1 shows the results.

EXAMPLE 19

Example 14 was repeated except that the raw material was changed to 10 g of 2-ethylnaphthalene and that the catalyst was changed to 200 mg of potassium phosphorus tungstate having a composition shown in Table 1. Table 1 shows the results.

EXAMPLE 20

Example 14 was repeated except that the alkylating agent was changed to propylene, that the catalyst was changed to 200 mg of potassium phosphorus tungstate having a composition shown in Table 1, and that the reaction temperature was changed to 170° C. Table 1 shows the results.

EXAMPLE 21

A 50 ml autoclave was charged with 10 g of naphthalene (desulfurized, purified product, supplied by Kawasaki Steel Corp.) and 10 ml of decane together with 200 mg of potassium phosphorus tungstate having a composition shown in Table 1, and the autoclave was closed. Then, air inside the autoclave was replaced with ethylene gas, and the mixture was allowed to react with stirring under an ethylene pressure of 30 kg/cm$^2$G at a temperature of 180° C. for 1 hour. After the reaction, the catalyst was separated by filtration, and the resultant reaction mixture was analyzed on its contents with gas chromatography using a capillary column (DB-1). Table 1 shows the results.

EXAMPLES 22-24

Example 14 was repeated except for the use of a metal salt of phosphorus tungstic acid having a composition shown in Table 1 (Examples 22 and 23) or phosphorus tungstic acid having a composition shown in Table 1 (Example 24). Table 1 shows the results.

TABLE 1

| Example | Catalyst | Catalyst amount (mg) | Reaction temperature (°C.) | Raw material conversion (%) | Selectivity to alkylation reactions (mol %) | Raw material | Alkylating agent |
|---|---|---|---|---|---|---|---|
| 14 | $K_{2.2}H_{0.8}PW_{12}O_{40}$ | 850 | 200 | 55 | 95 | naphthalene | ethylene |
| 15 | $Cs_{2.2}H_{0.8}PW_{12}O_{40}$ | 850 | 200 | 52 | 93 | naphthalene | ethylene |
| 16 | $K_2HPW_{12}O_{40}$ | 850 | 200 | 61 | 95 | naphthalene | ethylene |
| 17 | $KH_2PW_{12}O_{40}$ | 850 | 200 | 50 | 91 | naphthalene | ethylene |
| 18 | $K_2HPW_{12}O_{40}$ | 10 | 260 | 63 | 89 | naphthalene | ethylene |
| 19 | $K_2HPW_{12}O_{40}$ | 200 | 200 | 48 | 92 | 2-ethylnaphthalene | ethylene |
| 20 | $K_2HPW_{12}O_{40}$ | 850 | 170 | 65 | 97 | naphthalene | propylene |
| 21 | $K_{2.3}H_{0.7}PW_{12}O_{40}$ | 200 | 180 | 69 | 97 | naphthalene | ethylene |
| 22 | $K_{2.5}H_{0.5}PW_{12}O_{40}$ | 200 | 180 | 67 | 95 | naphthalene | ethylene |
| 23 | $K_{2.8}H_{0.2}PW_{12}O_{40}$ | 200 | 180 | 59 | 98 | naphthalene | ethylene |
| 24 | $H_3PW_{10}O_{40}$ | 850 | 200 | 43 | 85 | naphthalene | ethylene |

Note)
Selectivity to alkylation reactions stands for the total of selectivities to mono-, di-, tri- and tetra-alkylated products, and descriptions of crystal water of catalysts are omitted (this note also applies to Tables 2, 3 and 4 to be described later).

EXAMPLE 25

A 50 ml autoclave was charged with 10 g of naphthalene (purified naphthalene, supplied by Kawasaki Steel Corp.) and 10 ml of decane together with 850 mg of potassium silicotungstate having a composition shown in in Table 2, and the autoclave was closed. Then, air inside the autoclave was replaced with ethylene gas, and the mixture was allowed to react with stirring under an ethylene pressure of 30 kg/cm²G at a temperature of 200° C. for 2 hours. After the reaction the catalyst was separated by filtration, and the resultant reaction mixture was analyzed on its contents by gas chromatography. Table 2 shows the results.

EXAMPLE 26

Example 25 was repeated except for the use of potassium silicotungstate having a composition shown in Table 2. Table 2 shows the results.

EXAMPLE 27

Example 25 was repeated except that the catalyst was changed to 10 mg of silicotungstate having a composition shown in Table 2 and that the reaction temperature was changed to 260° C. Table 2 shows the results.

EXAMPLE 28

Example 25 was repeated except that the raw material was changed to 10 g of 2-ethylnaphthalene, that the catalyst was changed to 100 mg of potassium silicotungstate having a composition shown in Table 2. Table 2 shows the results.

EXAMPLE 29

Example 25 was repeated except for the use of 200 mg of cesium silicotungstate. Table 2 shows the results.

EXAMPLE 30

Example 25 was repeated except that the alkylating agent was changed to propylene, that the catalyst was changed to 200 mg of potassium silicotungstate having a composition shown in Table 2 and that the reaction temperature was changed to 170° C. Table 2 shows the results.

EXAMPLE 31

Example 25 was repeated except for the use of 850 mg of silicotungstungstic acid having a composition shown in Table 2. Table 2 shows the results.

TABLE 2

| Example | Catalyst | Catalyst amount (mg) | Reaction temperature (°C.) | Raw material conversion (%) | Selectivity to alkylation reactions (mol %) | Raw material | Alkylating agent |
|---|---|---|---|---|---|---|---|
| 25 | $KH_3SiW_{12}O_{40}$ | 850 | 200 | 45 | 97 | naphthalene | ethylene |
| 26 | $K_2H_2SiW_{12}O_{40}$ | 850 | 200 | 60 | 94 | naphthalene | ethylene |
| 27 | $K_2H_2SiW_{12}O_{40}$ | 10 | 260 | 35 | 91 | naphthalene | ethylene |
| 28 | $K_2H_2SiW_{12}O_{40}$ | 100 | 200 | 57 | 96 | 2-ethylnaphthalene | ethylene |
| 29 | $Cs_2H_2SiW_{12}O_{40}$ | 200 | 200 | 58 | 94 | naphthalene | ethylene |
| 30 | $K_2H_2SiW_{12}O_{40}$ | 200 | 170 | 53 | 98 | naphthalene | propylene |
| 31 | $H_4SiW_{12}O_{40}$ | 850 | 200 | 29 | 89 | naphthalene | ethylene |

EXAMPLE 32

A 500 ml round-bottomed flask was charged with 50 g of phosphorus tungstic acid ($H_3PW_{12}O_{40} \cdot 27H_2O$), and 100 g of water, and the phosphorus tungstic acid was dissolved in the water at room temperature. 2.0 Grams of potassium carbonate (special-degree reagent) was added to the solution with stirring. Thereafter, the mixture was subjected to an evaporation operation under reduced pressure with a rotary evaporator over a hot water bath at a temperature of 50° C. to give 45.6 g of potassium phosphorus tungstate.

FIG. 1 shows the pore distribution of the above potassium phosphorus tungstate. In FIG. 1, the ordinate axis shows the pore radius (r), and the abscissa axis shows the ratio (dv/d(log)r) of the infinitesimal change (dv) in pore volume to the infinitesimal change (d(log)r) in pore radius. The pore distribution was determined on the basis of the isothermal desorption curve of nitrogen gas at a liquid nitrogen temperature.

The above-obtained potassium phosphorus tungstate was used as a catalyst for the following reaction.

A 50 ml autoclave was charged with 10 g of naphthalene (desulfurized, purified product, supplied by Kawasaki Steel Corp.), 10 ml of decane and 200 mg of the above potassium phosphorus tungstate, and the autoclave was closed. Then, air inside the autoclave was replaced with nitrogen gas, and the mixture was allowed to react under an ethylene pressure of 30 kg/cm²G at a temperature of 180° C. for 1 hour. After the reaction, the catalyst was separated by filtration, and the resultant reaction mixture was analyzed to determine its components by gas chromatography. Table 3 shows the results.

EXAMPLES 33-35

Example 32 was repeated except for the use of a potassium phosphorus tungstate which had been prepared in the same manner as in Example 32 and had a composition shown in Table 3. Table 3 shows the results.

EXAMPLES 36-38

Figure 2:
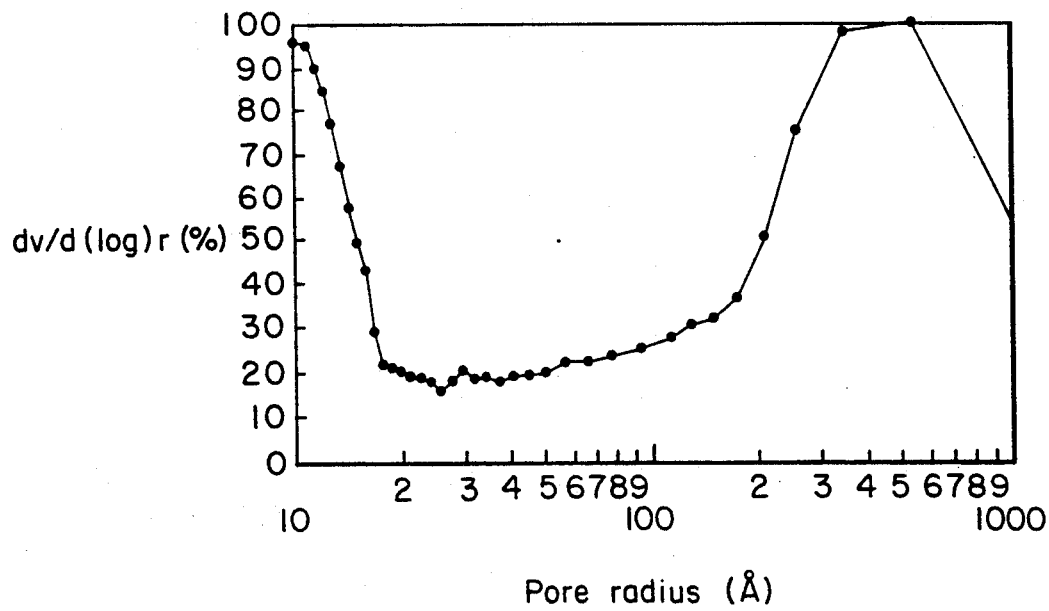
FIG. 2 is a pore distribution curve of the catalyst used in Example 38.

A potassium carbonate aqueous solution having a concentration shown in Table 3 was added to phosphorus tungstic acid aqueous solution to give a catalyst of potassium phosphorus tungstate shown in Table 3. Then, the reaction was carried out in the same manner as in Example 32. Table 3 shows the results. FIG. 2 shows the pore distribution of the catalyst used in Example 38.

TABLE 3

| Example | Potassium phosphorus tungstate (catalyst) | $K_2CO_3$ | Naphthalene conversion (%) | Amount of ethylation* (mmol/g · cat) |
|---|---|---|---|---|
| 32 | $HK_2PW_{12}O_{40}$ | solid | 65 | 360 |
| 33 | $H_{0.7}K_{2.3}PW_{12}O_{40}$ | solid | 69 | 404 |
| 34 | $H_{0.5}K_{2.5}PW_{12}O_{40}$ | solid | 71 | 419 |
| 35 | $H_{0.2}K_{2.8}PW_{12}O_{40}$ | solid | 59 | 328 |
| 36 | $HK_2PW_{12}O_{40}$ | 2% aqueous solution | 58 | 313 |
| 37 | $HK_2PW_{12}O_{40}$ | 10% aqueous solution | 61 | 327 |
| 38 | $H_{0.5}K_{2.5}PW_{12}O_{40}$ | 2.5% aqueous solution | 67 | 377 |

COMPARATIVE EXAMPLE 1

Example 1 was repeated except that the phosphorus tungstic acid was replaced with 200 mg of H+-ZSM5 which had been preliminarily dried under heat at 200° C.

The reaction results are as follows: Naphthalene conversion 0.1%, and selectivity to monoethylnaphthalenes 99%.

COMPARATIVE EXAMPLE 2

A 50 ml autoclave was charged with 700 mg of naphthalene, 100 mg of aluminum chloride and 2 ml of 1,2-dichloroethane. Then, ethylene was introduced into the autoclave under pressure until the ethylene pressure became 60 kg/cm²G, and the mixture was allowed to react with stirring at 30° C. for 5 hours.

The reaction results are as follows: Naphthalene conversion 49%, Selectivity to monoethylnaphthalenes 29%, selectivity to diethylnaphthalenes 18%, selectivity to triethylnaphthalenes 6%, and tar formation ratio 43%.

COMPARATIVE EXAMPLE 3

An attempt was made to repeat Example 1 by the use of 100 mg of p-toluenesulfonic acid in place of phosphorus tungstic acid. However, no reactions took place.

COMPARATIVE EXAMPLES 4-6

Example 14 was repeated except for the use of a catalyst shown in Table 4 and employment of the conditions shown in Table 4. Table 4 shows the results.

TABLE 4

| Example | Catalyst | Catalyst amount (mg) | Reaction temperature (°C.) | Raw material conversion (%) | Selectivity to alkylation reactions (mol %) | Raw material | Alkylating agent |
|---|---|---|---|---|---|---|---|
| 4 | AlCl₃ | 50 | 100 | 27 | 87 | naphthalene | ethylene |
| 5 | Silica alumina | 3,000 | 200 | 8 | — | naphthalene | ethylene |
| 6 | H—Y zeolite | 3,000 | 200 | 53 | 80 | naphthalene | ethylene |

What is claimed is:

1. A process for producing an alkyl-substituted naphthalene or naphthalene derivative, which comprises alkylating naphthalene or naphthalene derivative with an alkylating agent in the presence of a salt of a heteropoly-acid as a catalyst, said alkylating agent being selected from the group consisting of $C_2$-$C_{20}$ monoolefins and said salt of said heteropoly-acid being at least one compound selected from the group consisting of a compound of formula (1)

$$K_xH_{3-x}PW_{12}O_{40} \qquad (1)$$

wherein x is 0.5 to 2.8, and a compound of formula (2)

$$M_xH_{4-x}SiW_{12}O_{40} \qquad (2)$$

wherein M is a metal belong to the group Ia of the periodic table, and x is as defined above.

2. The process of claim 1, wherein the alkylating agent is an α-olefin.

3. The process of claim 1, wherein the catalyst comprises potassium phosphorus tungstate of the following formula (1)-1, $$K_xH_{3-x}PW_{12}O_{40} \qquad (1)-1$$

wherein x is as defined above, and has numerous pores having an average pore radius of 100 to 600 Å.

4. The process of claim 1, wherein M in the formula (2) is selected from the group consisting of potassium, rubidium and cesium.

5. The process of claim 1, wherein the catalyst is a product obtained by bringing a phosphorus tungstic acid aqueous solution and solid potassium carbonate into contact with each other.

6. The process of claim 1, wherein said naphthalene derivative is selected from the group consisting of methylnaphthalenes, dimethylnaphthalenes, ethylnaphthalenes, diethylnaphthalenes, trimethylnaphthalenes, isopropylnaphthalenes, and naphthalenes substituted with a combination of different alkyl groups.

7. The process of claim 1, wherein said naphthalene derivative is selected from the group consisting of 1-methylnaphthalene, 2-methylnaphthalene, 1,5-dimethylnaphthalene, 1,6-dimethylnaphthalene, 1-ethylnaphthalene, 2-ethylnaphthalene, 2,6-diethylnaphthalene, 2,3-diethylnaphthalene, 1,3,6-trimethylnaphthalenes, 1-isopropylnaphthalene, 2-isopropylnaphthalene, methylethylnaphthalene, methylisopropylnaphthalene, ethylisopropylnaphthalene, dimethylethylnaphthalene, methyldiethylnaphthalene, dimethyldiethylnaphthalene, dimethyldiisopropylnaphthalene, trimethylethylnaphthalene, trimethyldiethylnapthalene and diethylisopropylnaphthalene.

8. The process of claim 1, wherein said alkylating agent is selected from the group consisting of ethylene and propylene.

9. The process of claim 1, wherein said salt of said heteropoly-acid is supported on a support selected from the group consisting of silica gel, activated carbon, silica-alumina, alumina, saponite, montmorillonite, acid clay, activated clay, and titania.

10. The process of claim 6, wherein said alkylating agent is selected from the group consisting of ethylene and propylene.

11. The process of claim 7, wherein said alkylating agent is selected from the group consisting of ethylene and propylene.

* * * * *